United States Patent [19]

Maupetit et al.

[11] 4,083,812

[45] Apr. 11, 1978

[54] CERTAIN KETOALCOHOL TRICYCLIC NORSESQUITERPENE DERIVATIVES AND COMPOSITIONS CONTAINING THE SAME

[75] Inventors: Pierre Maupetit; Paul Jose Teisseire, both of Grasse, France

[73] Assignee: Societe Anonyme Roure Bertrand Dupont, Paris, France

[21] Appl. No.: 723,748

[22] Filed: Sep. 16, 1976

Related U.S. Application Data

[63] Continuation-in-part of Ser. No. 444,684, Feb. 21, 1974, Pat. No. 4,000,202.

[30] Foreign Application Priority Data

Feb. 28, 1973  Switzerland .................. 2884/73
Jul. 3, 1973  Switzerland .................. 9723/73

[51] Int. Cl.$^2$ .................. C07C 49/36; C07C 49/38; A61K 7/46
[52] U.S. Cl. .................. 252/522; 260/586 G
[58] Field of Search .................. 260/586 G, 617 F; 252/522

[56] References Cited

U.S. PATENT DOCUMENTS

| | | | |
|---|---|---|---|
| 3,923,899 | 12/1975 | Frater et al. | 260/586 G |
| 3,925,477 | 12/1975 | Frater et al. | 260/586 G |
| 3,996,169 | 12/1976 | Light et al. | 260/617 F |

*Primary Examiner*—Norman Morgenstern

*Attorney, Agent, or Firm*—Wallenstein, Spangenberg, Hattis & Strampel

[57] ABSTRACT

Odoriferous agents in the form of certain novel ketoalcohol tricyclic norsesquiterpene derivatives having the formulae

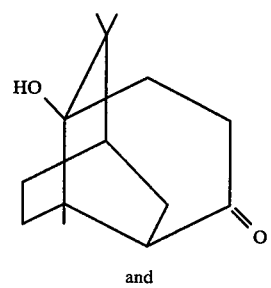

V and

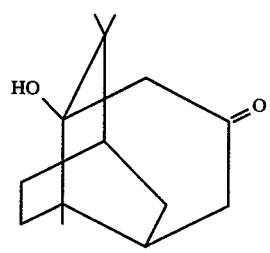

VII

2 Claims, No Drawings

CERTAIN KETOALCOHOL TRICYCLIC NORSESQUITERPENE DERIVATIVES AND COMPOSITIONS CONTAINING THE SAME

This application is a continuation-in-part of application Ser. No. 444,684, filed Feb. 21, 1974, now U.S. Pat. No. 4,000,202.

This invention is concerned with certain ketoalcohol tricyclic norsesquiterpene derivatives having the formulae

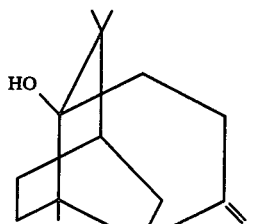

and

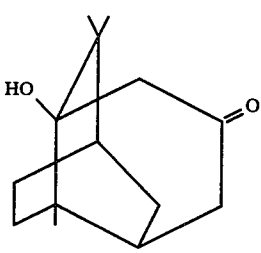

The foregoing compounds V and VII have been found to be useful as odorants and they are additionally useful as intermediates for the manufacture of the odorants. They also possess fixative properties. Their odour may be described as being camphorous, musty and woody. They can be combined in a manner known per se with other odorants to give particular odorant compositions (for example perfume bases), whereby the content of either or both of said compounds in such odorant compositions may vary within wide limits, for example between about 1 and 20 wt.%. Such odorant compositions can be used as perfumes or for the perfuming of cosmetic products (soaps, toilet waters, creams, etc.) as well as, for example, cleaning agents (detergents, washing agents, etc.).

The foregoing compounds can, as is set out in the following reaction schemes, be prepared as follows:

COMPOUND V (a) subjecting the unsaturated tricyclic alcohol norpatchoulenol (nordehydropatchoulol) of the following formula II to epoxidation for the preparation of an epoxy alcohol of the following formula III, (b) reducing an epoxy alcohol of said formula III for the preparation of a glycol of the following formula IV, (c) oxidising a glycol of said formula IV for the preparation of the aforesaid ketoalcohol tricyclic norsesquiterpene derivatives of the following formula V,

COMPOUND VII (d) subjecting the unsaturated tricyclic alcohol norpatchoulenol of the formula II to hydroboration and oxidation for the preparation of a glycol of the following formula VI, (e) oxidising said glycol of the formula VI for the preparation of the aforesaid ketoalcohol tricyclic norsesquiterpene derivative of the formula VII.

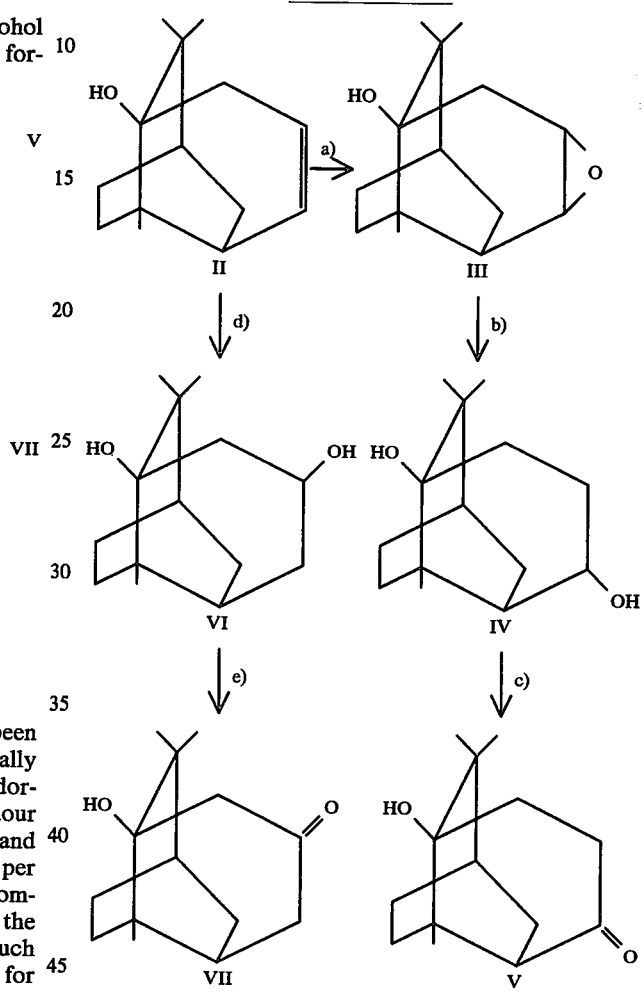

Reaction scheme

The unsaturated tricyclic alcohol (nordehydropatchoulol or norpatchoulenol), which serves as the starting material for the manufacture of the intermediate epoxy alcohol III and the intermediate glycol VI, is present in natural patchouli oil and can be isolated therefrom by known methods (c.f. French Pat. No. 7131577).

The epoxidation of norpatchoulenol II according to reaction (a) to produce the intermediate epoxy alcohol III can be carried out using a peracid such as perphthalic acid, perbenzoic acid or peracetic acid. The latter is preferred because of its ready availability.

The reduction of the epoxyalcohol III to the glycol IV according to reaction (b) can be carried out using organometal hydrides such as, for example, diisobutylaluminium hydride, lithium aluminum hydride, sodium bis(2-methoxy ethoxy) dihydridoaluminate, sodium ethyl dihydridoaluminate, and the like, in accordance with techniques utilizing organometal hydrides as reducing agents.

For the selective oxidation of the glycol IV to the ketoalcohol V according to reaction (c) a chromium trioxide/pyridine complex may be used as the oxidising agent.

For the preparation of the glycol VI from norpatchoulenol II according to reaction (d), as noted above, latter is subjected to hydroboration and oxidation. In course of this reaction, it has been found that certain amounts of the isomeric glycol IV also result.

The ketoalcohol VII may be prepared according to reaction (e) from the glycol VI by selective oxidation, for example, using techniques of the 2-phase selective oxidation process of Brown et. al. (J.A.C.S. 83 (1961), 2952) using chromic acid.

The invention will now be illustrated with reference to the following Examples. The letters (a), (b), (c), (d) and (e) are used, for convenience, to identify the same reaction steps which are indicated above.

EXAMPLE 1

(a) 1 g (4.8 mmol) of norpatchoulenol, dissolved in 50 ml of methylene chloride, and 1 g of dry sodium acetate are added to a 500 ml flask. The thus obtained suspension is stirred vigorously, cooled and then mixed with 15 ml of 35% peracetic acid. The mixture is then left for 48 hours at room temperature, until the norpatchoulenol has practically disappeared. After the addition of 300 ml of water, the reaction mass is extracted with methylene chloride. Then the organic extracts are washed with 9% sodium bicarbonate solution, 10% sodium sulphite solution and finally to neutrality with water. The solvent is then distilled off. There are thus obtained 1.05 g of crystallised, crude epoxyalcohol of the intermediate of formula III, which can be obtained analytically pure (90% yield) by chromatography on silica gel and vacuum sublimation and which then shows the following constants:

$[\alpha]_D^{25}$ (CHCl$_3$) = + 29.70

Mass Spectrum: C$_{14}$H$_{22}$O$_2$ (M = 222)

222(M); 207 (M—CH$_3$); 204 (M—H$_2$O); 189 (M—H$_2$O—CH$_3$);

179 (M—C$_3$H$_7$); 166; 161 (M—H$_2$O—C$_3$H$_7$); 138; 95; 84

IR-Spectrum:

$\nu_{max}^{KBr}$(cm$^{-1}$): 3520; 3620; 3460; 3000; 1465; 1380-1365; 1305; 1060-1040; 1030; 980; 950-870-810; 755; 740

NMR-Spectrum: (in δ units) 0.89; 1.01; 1.11; 2.80; 3.01.

(b) 100 ml of anhydrous petroleum ether and 10 ml of diisobutylaluminium hydride are added to a 500 ml flask provided with stirrer, reflux condenser and dropping funnel. The reaction medium is kept under a dry nitrogen atmosphere. Then 0.82 g (3.7 mmol) of the epoxyalcohol of formula III obtained according to part (a) of this Example 1, dissolved in 30 ml of dry petroleum ether, are added at ambient temperature to the hydride solution. After this addition, the reaction mixture is held under reflux for 3 hours, then cooled to approximately 0° C, slowly mixed with 20 ml of absolute ethyl alcohol and finally with 250 ml of saturated sodium chloride solution. The reaction mixture is extracted with petroleum ether, whereupon the organic extracts are washed to neutrality with water. Distillation of the solution produces 0.85 g of the glycol intermediate of formula IV. By chromatography on silica gel, there are obtained 0.80 g of white crystallised formula IV product (ca. 82% yield) with the following constants:

Mass Spectrum: C$_{14}$H$_{24}$O$_2$ (M = 224); 224 (M); 209 (M—CH$_3$); 206 (M—H$_2$O); 191 (M—H$_2$O—CH$_3$); 188 (M—2 H$_2$O); 181 (M—C$_3$H$_7$); 173 (M—2 H$_2$O—CH$_3$); 163 (206—C$_3$H$_7$); 149 (163—CH$_3$); 145 (163—H$_2$O).

IR-Spectrum: $_{max}^{KBr}$(cm$^{-1}$): 3420; 3000; 1465; 1380-1360; 1215; 1055; 985; 935; 905.

NMR-Spectrum: (in δ units) around 1.10; 3.80.

(c) 0.64 g (2.86 mmol) of the glycol of formula IV, obtained according to part (b) of this Example 1, are dissolved in 100 ml of methylene chloride. After the addition of 12 g of CrO$_3$/pyridine complex, the mixture is stirred for 5 hours at 20°-25° C, then filtered and the filtrate taken up in ethyl ether. The solution is washed with 10% hydrochloric acid to eliminate the pyridine, then with 9% bicarbonate solution, and finally until neutral with water. After distillation of the solvent, there are obtained 0.60 g of red, crystallised ketoalcohol of formula V, which is purified by chromatography over silica gel. Yield 0.53 g (ca. 85%). The pure product has the following constants:

Mass Spectrum: C$_{14}$H$_{22}$O$_2$ (M = 222): 222 (M); 207 (M—CH$_3$); 2204 (M—H$_2$O); 194,189; 179 (M—C$_3$H$_7$).

IR-Spectrum: $\nu_{max}^{KBr}$(cm$^{-1}$): 3460; 1700; 1420; 1385-1360; 1255; 1190; 1060-1045; 970; 775.

NMR-Spectrum: (in δ units) 0.83; 1.18 and 1.24 centred at 2.79.

Example 2

(d) 100 mg (0.48 mmol) of norpatchoulenol of formula I are dissolved in 100 ml of anhydrous tetrahydrofuran in a 50 ml flask. After cooling to 0° C, 3.5 ml of a solution of diborane in tetrahydrofuran are added in one portion thereto. The reaction mixture is then left to warm up to room temperature and left for 24 hours at this temperature. The organoborane formed is directly oxidised. For this purpose, 10 ml of an aqueous 3 N soda solution and 10 ml of 30% H$_2$O$_2$ are added thereto. The mixture is then stirred for 2 hours at normal temperature and then taken up in saturated sodium chloride solution. After extraction with ether and washing to neutrality, the solution is dried and the ether distilled off. There are thus obtained 100 mg of a crude mixture of the two glycols of formulae IV and VI in the form of a viscous, yellow product. This product mixture is chromatographed through a column of 20 g of silica gel, which enables the separation of the two glycols IV and VI. The glycol VI forms the main product of the reaction. Its constants are the following:

IR-Spectrum: $\nu_{max}$: 3460; 1390; 1360; 1075; 1025; 975; 960; 940 cm$^{-1}$

NMR-Spectrum: (p.p.m.); 0.73; 1.07; 1.20 and 4.20.

(e) 23 mg (0.1 mmol) of the glycol of formula VI, obtained according to part (d) of this Example 2, are dissolved in 5 ml of ether, stirred and then 0.5 ml of Brown's solution (J.A.C.S. 83 (1961), 2952) are added thereto at room temperature. The stirring is maintained for 18 hours. The mass is then taken up in water and extracted with ether. The ethereal solutions are washed to neutrality and the ether is distilled off. There is thus obtained crystallised ketoalcohol of formula VII, which is chromatographed over 5 g of silica gel and sublimed under a pressure of 0.5 mm Hg. Yield: 20 mg of white crystals (ca. 80%).

IR-Spectrum: $\nu_{max}$: 3626; 3525; 1695; 1420-1410; 1380-1360; 1075-1055; 1460; 1278; 1240; 1182; 1028; 970.

Illustrative odorant compositions containing the aforesaid compounds V and VII are shown below. All parts given are by weight.

EXAMPLE 3

SOAP COMPOSITION 100 parts of a conventional unperfumed toilet soap in the form of chips are mixed with 3 parts of the odorant compound of formula V to uniformly distribute said odorant compound into said soap chips.

EXAMPLE 4

| CLEANSING CREAM | |
| --- | --- |
| | Parts |
| Mineral Oil | 38 |
| Beeswax | 3 |
| Spermaceti | 3 |
| Propylene glycol | 3.5 |
| Self-emulsifying higher fatty acid monoglycerides | 13 |
| Compound of formula VII | 4 |
| Water | 38 |

The aforesaid composition is in form of an emulsion and is formulated in accordance with conventional procedures used in producing such emulsions.

EXAMPLE 5

| HAIR SHAMPOO | |
| --- | --- |
| | Parts |
| Lauryl sodium sulfate | 10 |
| Coconut oil fatty diethanolamides | 3 |
| Compound of Example V | 1.5 |

| HAIR SHAMPOO -continued | |
| --- | --- |
| | Parts |
| Compound of Example VII | 1.5 |
| Water | 84 |

What is claimed is:

1. Ketoalcohol tricyclic norsesquiterpene derivatives having the formulae

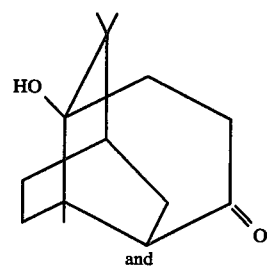

V and

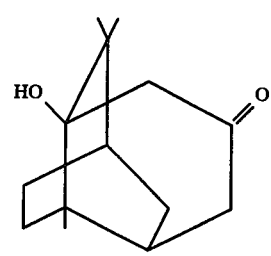

VII

2. An odoriferous composition containing an odoriferous amount of at least one odorant defined in claim 1.

* * * * *